US005562907A

United States Patent [19]
Arnon

[11] Patent Number: 5,562,907
[45] Date of Patent: Oct. 8, 1996

[54] METHOD TO PREVENT SIDE-EFFECTS AND INSENSITIVITY TO THE THERAPEUTIC USES OF TOXINS

[76] Inventor: Stephen S. Arnon, 9 Fleetwood Ct., Orinda, Calif. 94563

[21] Appl. No.: 254,238

[22] Filed: Jun. 6, 1994

Related U.S. Application Data

[63] Continuation-in-part of Ser. No. 62,110, May 14, 1993, abandoned.

[30] Foreign Application Priority Data

Mar. 8, 1994 [WO] WIPO ............... PCT/US94/02521

[51] Int. Cl.$^6$ .................. A61K 39/08; A61K 39/38; C07K 16/46
[52] U.S. Cl. .................. 424/236.1; 424/239.1; 424/542; 424/130.1; 424/141.1; 424/142.1; 424/150.1; 424/164.1; 424/167.1
[58] Field of Search .................. 424/130.1, 141.1, 424/142.1, 150.1, 164.1, 167.1, R39.1, 236.1, 542

[56] References Cited

U.S. PATENT DOCUMENTS

| | | | |
|---|---|---|---|
| 4,341,762 | 7/1982 | Haast | 424/88 |
| 4,689,299 | 8/1987 | Inseletal | 435/240.27 |
| 5,053,005 | 10/1991 | Bovodic | 604/51 |
| 5,183,462 | 2/1993 | Bovodic | 604/51 |

OTHER PUBLICATIONS

Bach et al (1993) Immunol. Today 14(9):421–424.

Arnon (1993) In "Botolinum and Tetanus Neurotoxeus: Neurotrossnussion and Biomedical Aspects" (Das Gypto, ed.) Plenum Press, N.Y., pp. 477–482, title & publ. pages.

Franz et al (1993) In "Botolinum and Tetanus Neurotoxnus: Neurotrossnussion and Biomedical Aspects" (Das Gupta, ed.) Plenum Press, N.Y., pp. 473–476, title & publ. pages.

Frankovich et al., "Clinical trial of botulism immune globulin for infant botulism" *The Western Journal of Medicine* (1991) 154(1):103.

"Clinical Use of Botulinum Toxin" Reprinted from: *NIH Consens. Dev. Conf. Consens. Statement* (Nov. 12–14, 1990), vol. 8, No. 8, pp. 1–20.

Hall et al., "Isolation of an Organism Resembling *Clostridium barati* Which Produces Type F Botulinal Toxin from an Infant with Botulism" *J. Clin. Microbiol.* (1985) 21(4):654–655.

Hatheway, "Bacteriology and Pathology of Neurotoigenic Clostridia" *Botulinum adn Tetanus Neurotoxins: Neurotransmission and Biomedical Aspects*, DasGupta, ed., Plenum Press, New York, 1993, pp. 491–502.

Aureli et al., "Two Cases of Type E Infant Botulism Caused by Neurotoxigenic *Clostridium butyricum* in Italy" *J. Infect. Dis.* (1986) 154(2):207–211.

Suen et al., "*Clostridium argentinense*, sp. nov: A Genetically Homogenous Group Composed of All Strains of *Clostridium botulinum* Toxin Type G and Some Nontoxigenic Strains Previously Identified as *Clostridium subterminale* or *Clostridium hastiforme*" *Int. J. System. Bacteriol.* (1988) 38(4):375–381.

Van Ermengem, "Ueber einem neuen anaëroben Bacillus und seine Beziehungen zum Botulismus" *Z. Hyg. Infektionskrankh.* (1897) 26:1–56. An English translation can be found in A New Anaerobic Bacillus and Its Relation to Botulism, *Rev. Infect. Dis.* (1979) 1(4):701–719.

Koening et al., "Clinical and Laboratory Observations on Type E Botulism in Man" *Medicine* (1964) 43:517–545.

Beller et al., "Repeated Type E Botulism in an Alaskan Eskimo" *N. Engl. J. Med.* (1990) 322(12):855.

Schroeder et al., "Botulism from Fermented Trout" *T. Norske Laegeforen* (1962) 82:1084–1086. An English translation, beyond the title, is currently not available.

Mandell et al., eds., *Principles and Practice of Infectious Diseases*, 3rd Edition, Churchill Livingstone, New York, (1990) pp. 1845.

Brin et al., "Localized Injections of Botulinum Toxin for the Treatment of Focal Dystonia and Hemifacial Spasm" *Adv. Neurol.* (1988) 50:599–608.

Jankovic et al., "Clinical Correlates of Response to Botulinum Toxin Injections" *Arch. Neurol.* (1991) 48:1253–1256.

Scott, "Clostridial Toxins as Therapeutic Agents" *Botulinum Neurotoxin and Tetanus Toxin*, Simpson, ed., Academic Press, Inc., New York, 1989, pp. 399–412.

Hambleton et al., "Antitoxins and Botulinum Toxin Treatment" *Brit. Med. J.* (1992) 304:959–960.

"Botulinum Toxin" *Lancet* (1992) 304:1508–1509.

Lees, "Botulinum toxin: Useful in adult onset focal dystonias" *Brit. Med. J.* (1992) 305:1169–1170.

Hatheway et al., "Immunogenicity of the Neurotoxins of *Clostridium botulinum*" *Therapy with Botulinum Toxin*, Jankovic et al., ed., Marcel Dekker, New York, 1993, pp. 93–107.

Schantz et al., "Properties and Use of Botulinum Toxin and Other Microbial Neurotoxins in Medicine" *Microbiol. Rev.* (1992) 56(1):80–99.

Scott, "Antitoxin Reduces Botulism Side Effects" *Eye* (1988) 2:29–32.

Black, et al., "Hypersensitivity Reactions Associated with Botulinal Antitoxin" *Am. J. Med.* (1980) 69:567–570.

Naik, "If the Product Becomes a Cosmetic, They Can Call It Bain de Botulism" *Wall Street Journal* (Nov. 6, 1992) p. B1.

(List continued on next page.)

Primary Examiner—Toni R. Scheiner
Attorney, Agent, or Firm—Morrison & Foerster

[57] ABSTRACT

Human-derived or human-compatible antitoxins are administered is an adjunct to therapy with a toxin, such as botulinum toxin or an immunotoxin, or as an adjunct to therapy with a combination of toxins, in order to reduce or prevent endogenous production of antibodies to the toxin(s) or other unwanted side-effects.

16 Claims, No Drawings

OTHER PUBLICATIONS

Creasy et al., eds., *Maternal–Fetal Medicine: Principles and Practice* (1989) 2nd Ed., W. B. Saunders Company, Philadelphia, Pennsylvania, 613–655.

Kamei et al., "Establishment of Stable Mouse/Human–Human Hybrid Cell Lines Producing Large Amounts of Anti–Tetanus Human Monoclonal Antibodies with High Neutralizing Activity" *Eur. J. of Epidem.* (1990) 6(4):386–397.

Leary, "Gains Reported in Transferring Genetic Material to Mice" *New Youk Times* (Mar. 30, 1993) p. B8.

Mariani et al., "A New Enzymatic Method to Obtain High–Yield F(ab)$_2$ Suitable for Clinical Use from Mouse IgG1" *Mol. Immunol.* (1991) 28(1/2):69–77.

Mittendorf et al., "RH$_0$(D) Immunoglobulin (RhoGAM): How It Came into Being" *Obstetrics and Gynecology* (1991) 77(2):301–303.

Stites et al., eds., *Basic and Clinical Immunology* (1991) 7th Ed., Appleton & Lange, Norwalk, Connecticut, pp. 291–292, 731–737.

Strauss et al., "Germ Line Transmission of a Yeast Artificial Chromosome Spanning the Murine $\alpha_1$(1) Collagen Locus" *Science* (1993) 259:1904–1907.

Tovey, "Haemolytic Disease of the Newborn and Its Prevention" *Brit. Med. J.* (1990) 300:313–316.

Anderson et al., "Botulinum Toxin Treatment of Spasmodic Torticollis" *Journal of the Royal Society of Medicine*, (1992) 85:524–529.

Gilman et al., eds. *The Pharmacologic Basis of Therapeutics* (1990) 8th Ed., Pergamon Press, New York. The title page and table of contents are enclosed herewith.

Schwarz et al., "Botulism immune globulin for infant botulism arrives –one year and a gulf war later" *The Western Journal of Medicine* (1992) 156(2):197.

Frankovich et al., "Clinical trial of botulism immune globulin for infant botulism" *The Western Journal of Medicine* (1991) 154(1):103.

Berkman et al., "Clinical Uses of Intravenous Immunoglobulins" *Ann. Int. Med.* (1990) 112:278–292.

McDonel, "*Clostridium perfringens* Toxins (type A,B,C,D, E)" *Pharmacol. Ther.* (1986) 10:617–655.

Ochs et al., "Survival of IgG Subclasses Following Administration of Intravenous Gammaglobulin in Patients with Primary Immunodeficiency Diseases" *Clinical Use of Intravenous Immunoglobulins*, Morell et al., eds., Academic Press, London, 1986, pp. 77–85.

Mankarious et al., "The Half–lives of IgG Subclasses and Specific Antibodies in Patients with Primary Immunodeficiency who are Receiving Intravenously Administered Immunoglobulin" *J. Lab. Clin. Med.* (1988) 112:634–640.

Smith, "Virulence Factors of *Clostridium Perfringens*" *Rev. Infect. Dis.* (1979) 1:254–260.

Lee, "Mode of Action of Cobra Venom and its Purified Toxins" Neuropoisons: Their pathophysiological actions Simpson, ed., Plenum Press, New York, 1971, pp. 21–70.

Greene et al., "Use of Botulinum Toxin type F injections to Treat Torticollis in Patients with Immunity to Botulinum Toxin Type A" *Movement Disorders* (1993) 8:479–483.

Carruthers et al., "Treatment of Glabellar Frown Lines with *C. botulinum* –A Exotoxin" *J. Dermatol. Surg. Oncol.* (1992) 18:17–21.

Lees et al., "Treatment of Cervical Dystonia Hand Spasms and Laryngeal Dystonia with Botulinum Toxin" *J. Neurol.* (1992) 239:1–4.

Vitetta et al., "Immunotoxins: Magic Bullets or Misguided Missiles?" *Immunology Today* (1993) 14:252–259.

Biro et al., "In vitroEffects of a Recombinant Toxin Targeted to the Fibroblast Growth Factor Receptor on Rat Vascular Smooth Muscle and Endothelial Cells" *Circ. Res.* (1992) 71:640–645.

Wawrzynczak et al., "Immunotoxins: the Power and the Glory" *Immunology Today* (1992) 13:381–383.

Wawrzynczak, "Systemic Immunotoxin Therapy of Cancer: Advances and Prospects" *Br. J. Cancer* (1991) 64:624–630.

Prior et al., "Barnase Toxin: A New Chimeric Toxin Composed of Pseudomonas Exotoxin A and Barnase" *Cell* (1991) 65:1017–1023.

Zeng et al., "Radioimmunotherapy for Unresectable Hepatocellular Carcinoma Using $I^{131}$–Hepama–1 mAb: Preliminary Results" *J. Cancer Res. Clin. Oncol.* (1993) 119:257–259.

Burrows et al., "Eradication of Large Solid Tumors in Mice with an Immunotoxin directed Against Tumor Vasculature" *Proc. Natl. Acad. Sci. USA* (1993) 90:8996–9000.

Amlot et al., "A Phase I Study of an Anti–CD22–Deglycosylated Ricin A Chain Immunotoxin in the Treatment of B–cell Lymphomas Resistant to Conventional Therapy" *Blood* (1993) 82:2624–33.

Soler–Rodriguez et al., "Ricin–A–Chain and Ricin A–Chain Immunotoxins Rapidly Damage Human Endothelial Cells: Implications for Vascular Leak Syndrome" *Exp. Cell Research* (1993) 206:227–234.

Pai et al., "Immunotoxin Therapy for Cancer" *JAMA* (1993) 269:78–81.

Skolnick, "First Immunotoxin Therapy for Many Common Solid Tumors Enters Phase 1 Clinical Trial" *JAMA* (1993) 270:2280.

Friedman et al., "Antitumor Activity of the Single–Chain Immunotoxin BR96 sFv–PE–40 Against Established Breast and Lung Xenografts" *J. Immunol.* (1993) 150:3054–3061.

Wang et al., "Polyethylene Glycol–Modified Chimeric Toxin Composed of Transforming Growth Factor Alpha and Pseudomonas Exotoxin" *Cancer Research* (1993) 53:4588–94.

Winter et al., "Humanized Antibodies" *Immunol. Today* (1993) 14:243–246.

Green et al., "Antigen–Specific Human Monoclonal Antibodies from Mice Engineered with Human Ig Heavy Light Chain YACs" *Nature Genetics* (1994) 7:13–21.

Lonberg et al., "Antigen–Specific Human Antibodies from Mice Comprising Four Distinct Genetic Modifications" *Nature* (1994) 368:856–859.

Rybak et al., "Humanization of Immunotoxins" *Proc. Natl. Acad. Sci* (1992) 89:3165–69.

Weller et al., "Cooperative Action of the Light Chain of Tetanus Toxin and the Heavy Chain of Botulinum Toxin Type A on the Transmitter Release of Mammalian Motor Endplates" *Neurosci. Letters* (1991) 122:132–134.

Olivera et al., "Conotoxins: Peptide Ligands for Receptors and Ion Channels" *Toxicon.* (1994) 32:244.

Uchitel et al., "Characterization of Calcium Channels Involved in Transmitter Release at the Mammalian Neuromuscular Junction" *Toxicon* (1994) 32:240–41.

Cull–Candy et al., "Effects of Botulinum Toxin on Neuromuscular Transmission in the Rat" *J. Physiol.* (1976) 260:177–203.

Kameyama et al., "Purification and Some Properties of Kappa Toxin of *Clostridium perfringens*" *Japan J. Med. Sci. Biol.* (1971) 24:9–23.

Matsushita et al., "Purification and Characterization of a *Clostridium perfringens* 120-kilodalton Collagenase and Nucleotide Sequence of the Corresponding Gene" *J. Bacteriol.* (1994) 176:149–56.

Smith, "Clostridium histolyticum" *The Pathogenic Anaerobic Bacteria*, second edition, Charles C. Thomas, Springfield, IL, (1975) pp. 284–287.

Mookhtiar et al., "*Clostridium histolyticum* Collagenases: A New Look at Some Old Enzymes" *Matrix* (1992) I Supp. 1:116–126.

Youle et al., "Cytotoxic Ribonucleases and Chimeras in Cancer Therapy" *Critical Reviews Therapeutic Drug Carrier Systems* (1993) 10:1–28.

METHOD TO PREVENT SIDE-EFFECTS AND INSENSITIVITY TO THE THERAPEUTIC USES OF TOXINS

REFERENCE TO RELATED APPLICATION

This application is a continuation-in-part of U.S. patent application Ser. No. 08/062,110 filed on May 14, 1993, now abandoned. That application is incorporated by reference.

TECHNICAL FIELD

In general, this invention relates to use of human immune globulin or other human compatible antibodies as an adjunct to toxin therapy. In one embodiment, the invention relates to the treatment of disorders for which botulinum toxin(s) are used therapeutically.

BACKGROUND OF THE INVENTION

Therapeutic Use of Botulinum Toxin

The clostridial neurotoxins consist of the botulinum toxins, the botulinum-like toxins and tetanus toxin. Botulinum neurotoxin is a protein molecule that is produced by the bacterium *Clostridium botulinum*, and it is considered to be the most deadly poison known. (Gill, M. D., "Bacterial toxins: a table of lethal amounts" *Microbiol. Rev.* (1982) 46: 86–94.) *Clostridium botulinum* is the species name assigned to four metabolically diverse groups of anaerobic bacteria whose one common feature is the production of botulinum neurotoxin. Seven different antigenic variants of the botulinum neurotoxin molecule are presently known and are serologically distinguishable from each other by means of monovalent antitoxin antibodies. These different toxin types have arbitrarily been assigned the letters A through G. Botulinum toxin produces muscle paralysis and relaxation by blocking the motoneuron from releasing acetylcholine at the neuromuscular junction. This effect derives from the enzymatic action of the "light" (50,000 MW) chain of botulinum toxin, the various types (A–G) of which hydrolyze key proteins which the motoneuron relies on for the release of the acetylcholine-containing vesicles that trigger muscle contraction. In addition, the "light" chain of tetanus neurotoxin is a protease that acts identically to botulinum type B. (Huttner, W. B., "Snappy Exocytoxins" *Nature* (1993) 365: 104–105). The substrate proteins for the clostridial neurotoxins are components of the synaptic vesicle "docking" or "fusion" complex and are known by their acronyms VAMP, SNAP-25 and syntaxin (Barinaga, M., "Secrets of Secretion Revealed" *Science* (1993) 260: 487–489). The relationships between these substrates and the botulinum and tetanus toxins are shown in Table 1 below.

TABLE 1

| Light Chain Substrates | | |
| --- | --- | --- |
| (1) VAMP | (2) SNAP-25 | (3) Syntaxin |
| type B | type A | type C |
| type D | type E | |
| type F | | |
| type G | | |
| tetanus | | |

The properties of botulinal toxins have allowed them to be used therapeutically. Botulinum toxin is used to produce a temporary muscle paralysis in diseases characterized by: 1) overactivity of a particular muscle or muscle group (e.g., strabismus); 2) involuntary muscle spasm (the dystonias); and 3) other disorders of movement. Numerous therapeutic uses for botulinum toxin were addressed at a November 1990 National Institutes of Health Consensus Development conference. The consensus panel from this conference resolved that botulinum toxin therapy is safe and effective for treating strabismus, blepharospasm, hemifacial spasm, adductor spasmodic dysphonia, jaw-closing oromandibular dystonia, and cervical dystonia. (Clinical Use of Botulinum Toxin. (Reprinted from *NIH Conses. Dev. Conf. Consens. Statement* 1990 Nov 12–14; 8(8)) Because the effects of the toxin last for only a few months, repeated injections of toxin are necessary to sustain its therapeutic benefit for chronic conditions.

In December 1989, the U.S. Food and Drug Administration (FDA) licensed for medicinal use a crystalline preparation of botulinum type A toxin, OCULINUM® toxin (also designated BOTOX® toxin, Allergan, Inc., Irvine, Calif.). OCULINUM® toxin contains botulinum neurotoxin, other bacterial protein molecules that co-crystallized with the neurotoxin, and stabilizing materials. OCULINUM® toxin is typically used to treat diseases such as strabismus, blepharospasm, hemifacial spasm, adductor spasmodic dysphonia, jaw-closing oromandibular dystonia and cervical dystonia.

Because the various botulinum and tetanus toxin light chains (proteases) have different substrates within the motoneuron cytosol, several two-fold and three-fold type combinations are therapeutically beneficial. There are three groupings of two-fold combinations. First, any toxin listed in column (1) of the above table can be combined with any toxin listed in column (2); second, column (3) (i.e., type C toxin) can be combined with any toxin in column (1); and third, column (3) can be combined with any toxin in column (2). The beneficial three-fold combinations all contain type C toxin. Type C toxin can be combined with either type A or type E toxin and the resulting combination can then be combined with any of the toxins in column (1). These 10 combinations consist of ABC, ADC, AFC, AGC, A-tetanus-C, EBC, EDC, EFC, EGC, and C-E-tetanus.

Additionally, a number of organisms producing botulinum-like toxins have been identified. For example, a unique strain of *Clostridium baratii* produces a type F-like toxin, and a unique strain of *Clostridium butyricum* produces a type E-like toxin.

Initially it was believed that individuals exposed to botulinum toxin did not produce antibodies against the toxin, due to the phenomenal potency of the toxin. It was thought that an immunogenic dose of the toxin would be lethal, i.e., that the amount of toxin needed to induce antibody production exceeded the lethal dose. This belief derived from decades of experience with foodborne botulism.

*Clostridium botulinum* and its toxin were first described as the cause of foodborne botulism in 1897. (Van Ermengem E., "Ueber einem neuen anaeroben Bacillus und seine Beziehungen zum Botulismus" *Z. Hyg. Infektionskrankh.* (1897): 26: 1–26. English translation, *Rev. Infect. Dis.* (1979) 1: 701–19.) Based on the experience with foodborne botulism, it had been determined that no antibodies developed in patients who survived the illness, even among patients who were so ill that they required mechanical ventilation for survival. (Koenig, M. G., et al., "Clinical and Laboratory Observations on Type E Botulism in Man" *Medicine* (1964) 43: 517–45) Consistent with this understanding, it had been reported that patients who recovered from either type B or type E foodborne botulism later experienced a second occurrence of foodborne botulism caused by the same toxin type. (Beller, M. and Middaugh, J. P., "Repeated type E botulism in an Alaskan Eskimo" *N. Engl. J. Med.* (1990) 322: 855; Schroeder, K., Tollefsrud, A. L., "Botulism from Fermented Trout" *T. Norske Laegeforen* (1962) 82: 1084–87) These reports were used to support the conclusion that exposure to minute, disease-causing amounts of botulinum toxin did not result in the development of antibodies to the toxin.

The failure of the immune system to make antibodies when exposed to botulinum toxin through illness was considered to be analogous to the experience with the human illness tetanus. Tetanus results from the effects of a neurotoxin (tetanospasmin) produced in infected wounds by *Clostridium tetani*, a member of the same bacterial genus as *Clostridium botulinum*. Of all known toxins, tetanospasmin is second only to botulinum toxin in potency. (Gill, M. D., "Bacterial Toxins: A Table of Lethal Amounts" *Microbiol. Rev.* (1982) 46: 86–94) Experience with tetanus had shown that "the quantity of tetanospasmin required to produce tetanus is insufficient to induce a protective immune response, and patients with this disease require a primary immunization series." (Mandell, G. L., Douglas, R. G., Bennett, J. E. eds., *Principles and Practice of Infectious Diseases*, 3d ed., Churchill Livingstone, N.Y., (1990) at p. 1845). Thus, with botulism as with tetanus, it was understood that an immunogenic dose of toxin exceeded the lethal dose.

However, in the context where botulinum toxin is used therapeutically, a new picture has developed. It has been observed that some patients who initially benefitted from the toxin, later became insensitive (refractory, resistant) to its use. This insensitivity has been attributed to the development, upon repeated injections with the toxin, of antibodies against the toxin.

Evidence that patients were developing neutralizing antibodies against the toxin after repeated treatments, thereby becoming unresponsive to the therapeutic effects of the toxin, began to emerge in the late 1980's. Brin and colleagues in 1988 reported that two of 90 patients they studied had developed antibodies to botulinum toxin and had become refractory to treatment (Brin, M. F., et al., "Localized Injections of Botulinum Toxin for the Treatment of Focal Dystonia and Hemifacial Spasm" *Adv. Neurol.* (1988) 50: 599–608) Jankovic and Schwartz obtained sera from 14 patients characterized as "non-responders" to botulinum toxin therapy, and found neutralizing antibodies against the toxin in 5 (37.5%); no antibodies were found in 32 patients characterized as "responders" to the toxin (P<0.0001). (Jankovic, J., Schwartz, K. S., "Clinical correlates of response to botulinum toxin injections" *Arch. Neurol.* (1991) 48: 1253–56) The patients with antibodies had, on average, received approximately twice as much toxin [1600 U, range 500–2450] as had the patients without antibodies [891 U, range 100–2150]. Additionally, Scott identified seven dystonia patients who had become refractory to treatment; all had neutralizing antibodies present in their sera. (Scott, A. B., "Clostridial Toxins as Therapeutic Agents" pp. 399–412 in Simpson, L. L., ed. *Botulinum neurotoxin and tetanus toxin*, Academic Press, NY (1989)) Six of the patients in the Scott study had received 300–400 ng and one only 100 ng of toxin within a 30-day period. (For clinical purposes, 1 ng of OCULINUM® toxin equals approximately 2.5–3.0 U.)

In England, Hambleton and colleagues studied 20 patients categorized as "maintained response" or as "diminished response." (Hambleton, P., Cohen, H. E., Palmer, B. J., Melling, J., "Antitoxins and botulinum toxin treatment" *Brit. Med. J.* (1992) 304: 959–60 at 959) These patients were selected from a group of several hundred spasmodic torticollis patients who had been treated for several years with botulinum type A toxin. Seven (35%) of the patients studied were found to have toxin-neutralizing antibodies that considerably diminished or abolished their therapeutic response to the toxin.

The American and British findings are especially notable when taken together, since the British investigators used a preparation of botulinum toxin that was made in England, in contrast to the preparation that is both made and used in the United States. Hence, neutralizing antibodies have arisen in patients irrespective of whether the British or American preparation of botulinum toxin was used.

Heretofore, the research emphasis concerning the therapeutic use of botulinum toxin has focused on development of more highly purified toxins as a means to control the immune response.

The focus on developing more highly purified toxins has been noted by two editorials from late 1992, editorials that overviewed the therapeutic use of botulinum toxin. One editorial appeared in the Dec. 19/26, 1992 issue of the Lancet ("Botulinum Toxin" *Lancet* (1992) 2: 1508–9), and the other was published Nov. 14, 1992 in the *British Medical Journal* (Lees, A. J., "Botulinum Toxin: Useful in Adult Onset Focal Dystonias" *BMJ* (1992) 305: 1169–70 at p.1170).

The Lees editorial, noted that "[p]atients have continued to respond with benefit for more than five years, although antibodies to the toxin may develop in the peripheral blood, leading to initial unresponsiveness or late resistance (Lees, A. J., "Botulinum Toxin: Useful in Adult Onset Focal Dystonias" *BMJ* (1992) 305: 1169–70 at p. 1170). The Lees editorial concluded stating, "Trials of other types of botulinum toxin are under way, and more effective toxins capable of producing longer durations of benefit without inevitably increasing unwanted effects may be developed in the near future." Thus, the proposed solution to the problem of antibody formation and resultant insensitivity was to increase the purity of the toxins used or to develop the other botulinum toxin serotypes (e.g., B, C, D etc.).

The *Lancet* editorial states "Although the toxin moiety itself is known to be antigenic, toxin neutralizing antibodies could also arise from other parts of the BtA-hemagglutinin complex, so a different preparation of BtA [botulinum toxin type A] might be worth trying. A purer form of BtA would allow us to explore this possibility." (Editorial, "Botulism Toxin" *Lancet* (1992) 3: 1508–09 at p.1508). Again, the proposed solution to the problem of antibody formation was to increase the purity of the toxin preparations injected into patients.

Notably, neither of these reviews discloses nor suggests the possibility of using 1) a human-derived botulism immune globulin; 2) which immune globulin would be injected intravenously; 3) in order to prevent the unwanted side effects of toxin diffusion and antitoxic antibody formation in treated patients.

A detailed discussion regarding the development of antibodies to botulinum toxin in toxin-treated patients was reported by Hatheway and Dang. (Hatheway, C. L., Dang, C., "Immunogenicity of the Neurotoxins of Clostridium botulinum" in Jankovic, J., Hallet, M. eds. *Therapy with Botulinum Toxin*, Marcel Dekker, New York, N.Y. (1993)) Eighty-eight patients in the U.S. were followed for one year after they began treatment with toxin, during which time the amount of toxin received ranged from 0 to 2550 units. At one year into treatment, 29 patients (33%) had developed neutralizing antibody against the toxin. The antibody-positive patients had received an average of 1051 t.u. of toxin, while the antibody-negative patients had received an average of 301 t.u., again suggesting a dose-response effect in the induction of antibody. This dose-response possibility was borne out when the patients were stratified according to dose received: <500 treatment units, 4% with antibody; 500–1000 treatment units, 45% with antibody; 1000–2000 treatment units, 83% with antibody; >2000 treatment units, 100% with antibody. In addition, Hatheway and Dang noted that continued treatment of patients who have subdetectable levels of antibodies might serve to boost the antitoxin titers above the minimum demonstrable level.

Patients who require botulinum toxin injections generally must have the injections repeated at regular intervals. Dose-response data, such as that of Hatheway and Dang, suggest that as the duration of currently practiced botulinum toxin treatment is extended, more patients will develop antibody and thereby lose the therapeutic benefit of the toxin. For this reason some expert physicians recommend limiting patients with dystonia to four injections per year, even if the beneficial effect of injected botulinum toxin lasts less than three months (Lees, A. J. et al., "Treatment of Cervical Dystonia Hand Spasms and Laryngeal Dystonia with Botulinum Toxin" *J. Neurol.* (1992) 239: 1–4).

Antibody development also limits the potential to administer combinations of botulinum toxin serotypes. In this regard, the current practice holds that patients should be treated with just one toxin type at a time, so that if and when antibodies to that toxin type develop, the patient can be changed to a different, single toxin type. To illustrate, patients who had been treated with botulinum type A toxin and developed neutralizing antibodies to it were shifted to treatment with botulinum type F toxin (Greene, P. E. and Fahn, S., "Use of Botulinum Toxin Type F Injections to Treat Torticollis in Patients with Immunity to Botulinum Toxin Type A" *Movement Disorders* (1993( 8: 479–83).

Although the problem of antibody development with botulinum toxin therapy has not been successfully addressed, other problems with the toxin therapy have been studied. It has been noted that patients injected with botulinum toxin have suffered complications due to the apparent diffusion of the toxin from the injected muscle(s) to adjacent muscles. For example, complications have included drooping eyelids (to the extent that vision is blocked), and difficulty with swallowing (to the extent that hospitalization was needed in order that a stomach feeding tube could be placed). (Jankovic, J., Brin, M. F., "Therapeutic Uses of Botulinum Toxin" *N. Engl. J. Med.* (1991) 324: 1186–94; Schantz, E. J., Johnson, E. A., "Properties and Use of Botulinum Toxin and other Microbial Neurotoxins in Medicine" *Microbiol Revs.* (1992) 56: 80–99) In certain clinical situations, such as with small or vitally-placed muscles, diffusion (or "leaking" of toxin) has limited the amount of toxin that could otherwise have been therapeutically injected, because of concern that such side-effects would develop. (Clinical Use of Botulinum Toxin. (Reprinted from *NIH Conses. Dev. Conf. Consens. Statement* 1990 Nov. 12–14; 8(8) ); Jankovic, J., Brin, M. F., "Therapeutic Uses of Botulinum Toxin" *N. Engl. J. Med.* (1991) 324: 1186–94; Scott, A. B., "Clostridial Toxins as Therapeutic Agents" pp. 399–412 in Simpson, L. L., ed. *Botulinum Neurotoxin and Tetanus Toxin*, Academic Press, NY (1989); Scott, A. B., "Antitoxin reduces botulinum side effects" *Eye* (1988) 2: 29–32)

In certain situations the amount of botulinum toxin that can be injected is limited by anatomical considerations and the tendency of the injected toxin to diffuse away from the injection site. In particular, injection of toxin into dystonic muscles in the upper neck or in the back of the tongue must be limited in order to avoid paralyzing the gag reflex and the swallowing muscles. If these muscles are made flaccid by toxin that has diffused into them, then the patient may become unable to eat or unable to keep oral secretions from draining into the lungs. Also, the amount of toxin that can be injected into facial or eye muscles (e.g., for blepharospasm) is limited by the toxin's ability to diffuse into adjacent muscles (e.g., eyelid or oculomotor). When such diffusion occurs, the resulting muscle paralysis can cause double vision or ptosis so severe that sight is obstructed by the drooping eyelid. In general, these complications are considered unacceptable.

An experimental attempt to overcome the side-effect of toxin diffusion into adjacent muscles was attempted by Scott. (Scott, A. B., "Antitoxin reduces botulinum side effects" *Eye* (1988) 2: 29–32) Scott's effort utilized direct intramuscular injection of equine botulinum antitoxin. The antitoxin was injected into the toxin-treated muscles or into untreated adjacent eye muscles. At the time Scott did his clinical studies with antitoxin, the botulinum antitoxin was a horse-derived product available from Connaught Laboratories (Toronto, Canada).

In Scott's method of direct intramuscular injection of horse-derived antitoxin, Scott addressed only one of the fundamental problematic issues with botulinum toxin therapy: diffusion of toxin to adjacent muscles. Antibody development consequent to botulinum toxin use was neither contemplated nor addressed. Because of clinically observed weakness in muscles adjacent to those injected, Scott mentioned a theoretical possibility of intramuscular use of human-derived antitoxin: "A human-derived ATX [antitoxin] and the non-toxic large fragment of the toxin molecule to block unwanted toxin binding are additional related techniques to reduce side effects and to increase efficacy which we are pursuing and which avoid the theoretical risks of immunity or sensitisation [sic] to equine-derived proteins" (Scott A. B., "Antitoxin Reduces Botulinum Side Effects" *Eye* (1988) 2: 29–32 at p. 32) Again, however, this proposal for further study was set out in the context of intramuscular antitoxin injection, with a goal of controlling toxin diffusion.

Although Scott might have been interested in using human botulism immune globulin (BIG) for intramuscular injections, he was unable to do so. At the time of Scott's study, the U.S. Army had the world's only supply of BIG. Also, at that time, it was not yet known that some patients injected therapeutically with botulinum toxin would develop antibodies to it. Scott's concern addressed only the possibility of development of antibodies to the equine botulism antitoxin.

Scott's approach was clinically unsatisfactory because it required the injection of additional muscles besides those targeted for the toxin (requiring additional physician/patient time and risk), and because the horse-derived botulinum antitoxin was a foreign protein capable of stimulating antibody production against itself when injected into humans. Hence, with repeated use, patients given the horse-derived antitoxin can be expected to develop antibodies against it and also to become refractory to its effects, just as some patients have become refractory to the effects of injected botulinum toxin. Of further concern, the horse-derived botulinum antitoxin is known to provoke severe allergic complications when used to treat patients with food-borne botulism: approximately one in eight such patients experienced anaphylaxis or serum sickness (i.e., allergic shock or kidney damage). (Black, R. E., Gunn, R. A., "Hypersensitivity Reactions Associated with Botulinal Antitoxin" *Am. J. Med.* (1980) 69: 567–70)

In addition to its accepted usage for the treatment of strabismus and various dystonias, botulinum toxin has also been used to reduce facial wrinkles by temporarily weakening the underlying muscles. (Carruthers, J. D. A. and Carruthers, J. A., "Treatment of Glabellar Frown Lines with *C. botulinum*-A exotoxin" *J. Dermatol. Surg. Oncol.* (1992) 18: 17–21) If this cosmetic procedure finds widespread use, then based on the incidence of the dystonias in the general population, it is predicted that among the population cosmetically treated with botulinum toxin, some individuals will eventually experience the onset of a dystonia. For these patients to then be able to therapeutically benefit from injection of botulinum toxin, it is important that they would not have developed neutralizing antibodies against the toxin during their cosmetic treatment with it.

Therapeutic Use of Chimeric Toxins, Recombinant Toxins and Immunotoxins

Chimeric toxins, recombinant toxins, and immunotoxins are a relatively new group of macromolecules that are being developed for use in a variety of human illnesses. The underlying therapeutic principle is the joining of a toxin molecule to a targeting molecule of high specificity. The targeting molecule then delivers the toxin to the unwanted cell or tissue, where the toxin portion of the molecule is internalized and poisons the cell. Chimeric toxins, recombinant toxins, and immunotoxins are potentially useful in the treatment of cancer (both solid tumors and hematological malignancies), autoimmune diseases (e.g., rheumatoid arthritis and diabetes mellitus type 1), and other conditions such as Acquired Immunodeficiency Syndrome (AIDS), graft versus host disease (GVHD), vascular restenosis, and rejection of organ transplants (Vitetta, E. S. et al., "Immunotoxins: Magic Bullets or Misguided Missiles? *Immunology Today* (1993) 14: 252–259; Biro, S. et al., "In vitro Effects of a Recombinant Toxin Targeted to the Fibroblast Growth Factor Receptor on Rat Vascular Smooth Muscle and Endothelial Cells" *Circ. Res.* (1992) 71: 640–5; and Wawrzynczak, E. J. and Derbyshire, E. J. "Immunotoxins: the Power and the Glory" *Immunology Today* (1992) 13: 381–383).

Targeting molecules utilized to convey various toxins include monoclonal antibodies and antibody fragments, growth factors (e.g., epidermal growth factor), cytokines (e.g., interleukin-2), and plant lectins. The principal toxins (or their fragments) used currently are bacterial or plant in origin and include ricin, diphtheria toxin and Pseudomonas exotoxin A (Vitetta, E. S. et al., "Immunotoxins: Magic Bullets or Misguided Missiles? *Immunology Today* (1993) 14: 252–259; and Wawrzynczak, E. J. and Derbyshire, E. J. "Immunotoxins: the Power and the Glory" *Immunology Today* (1992) 13: 381–383). Other plant and fungal toxins (e.g., gelonin, saporin) known as "ribosome-inactivating-proteins" have had their genes cloned in preparation for possible use as immunotoxins. Ribosome-inactivating proteins are advantageous toxins because they are single-chain, low molecular weight proteins (Wawrzynczak, E. J., "Systemic Immunotoxin Therapy of Cancer: Advances and Prospects" *Br. J. Cancer* (1991) 64: 624–630). A chimeric toxin comprised of two distinct toxins from different bacterial species has been evaluated experimentally (Prior, T. I. et al., "Barnase Toxin: A New Chimeric Toxin Composed of Pseudomonas Exotoxin A and Barnase" *Cell* (1991) 65: 1017–23). One interesting immunotoxin used clinically contained a radioisotope as its passenger toxin (Zeng, Z C et al., "Radioimmunotherapy for Unresectable Hepatocellular Carcinoma Using $I^{131}$-Hepama-1 mAb: Preliminary Results" *J. Cancer Res. Clin. Oncol.* (1993) 119: 257–9).

Although immunotoxins are still in the early stages of clinical evaluation as therapeutic agents, a number of problems that limit their utility have become evident. These problems include the complications and side-effects of 1) immunogenicity, 2) hepatotoxicity, 3) cross-reactivity with and injury to normal tissue (e.g., stomach, nerve, muscle), 4) injury to vascular endothelium, resulting in the "vascular leak" syndrome, and 5) instability, resulting in free toxin in the body. In addition, treatment of solid tumors (e.g., lung, breast, liver) with immunotoxins has been less satisfactory than treatment of hematological malignancy (e.g., leukemia) because of practical problems related to the large bulk of solid tumors and the anatomical difficulty of delivering an immunotoxin molecule to all tumor cells. New methods that overcome or circumvent these problems are needed if immunotoxins are to become useful therapeutic tools.

A variety of approaches to overcome these clinical obstacles have been tried. The instability that results from using a chemical linkage (e.g., sulfhydryl bonding) between toxin and antibody has been improved by moving to the covalent peptide-bond linkage of the recombinant toxin. Potential cross-reactivity is minimized by selecting the most highly specific antibody or lectin available, after screening in vitro in rodents and in primates. Nonetheless, cross-reactivity of immunotoxins with normal tissues remains a clinical problem. In the case of ricin A-chain toxins, hepatotoxicity resulted from toxin-associated oligosaccharides binding directly to liver cells and was circumvented by eliminating the oligosaccharides from ricin. Bacterial toxins and ribosome-inactivating-proteins cause hepatotoxicity by binding to non-carbohydrate hepatocyte receptors or by binding to serum proteins that have receptors in the liver, and solutions to this form of hepatotoxicity have not yet been found. To improve the efficacy of immunotoxins against solid tumors, targeting of the immunotoxin antibody to unique antigens expressed in the tumor's vasculature, with consequent interruption of the tumor's blood supply, has been accomplished in experimental animals (Burrows, F. J. and Thorpe, P. E., "Eradication of Large Solid Tumors in Mice with an Immunotoxin Directed Against Tumor Vasculature" *Proc. Natl. Acad. Sci. USA* (1993) 90: 8996–9000).

The "vascular leak syndrome" consists of edema, decreased serum albumin and weight gain that results either directly or indirectly from immunotoxin-mediated injury to the vascular endothelium and increased vascular permeability. When the leakage occurs in the lungs, the resultant pulmonary edema can be life-threatening (Amlot, P. L. et al., "A Phase I Study of an Anti-CD22-Deglycosylated Ricin A Chain Immunotoxin in the Treatment of B-cell Lymphomas Resistant to Conventional Therapy" *Blood* (1993) 82: 2624–33). In an experimental system using human umbilical endothelial cells, "rapid and dramatic" morphological changes consisting of cell rounding with gap formation were seen one hour after exposure to a ricin-A chain immunotoxin, while inhibition of protein synthesis was not observed until four hours after exposure (Soler-Rodriguez, A. M. et al., "Ricin A-Chain and Ricin A-Chain Immunotoxins Rapidly Damage Human Endothelial Cells: Implications for Vascular Leak Syndrome" *Exp. Cell Research* (1993) 206: 227–34). There is presently no circumvention for the "vascular leak syndrome," in part because its mechanism remains obscure.

A major limitation to the effectiveness of immunotoxin therapy is the problem of immunogenicity. Patients treated with immunotoxins rapidly develop their own antibodies against one or both (usually both) portions of the immunotoxin molecule, often within two weeks of starting immunotoxin therapy (Pai, L. H. and Pastan, I., "Immunotoxin Therapy for Cancer" *JAMA* (1993) 269: 78–81; and Skolnick, A. A., "First Immunotoxin Therapy for Many Common Solid Tumors Enters Phase I Clinical Trial" *JAMA* (1993) 270: 2280). A recent summary of 15 clinical trials with immunotoxins in which antibody induction was studied determined that in 12 (80%) of the trials, at least 50% of patients developed antibodies against the immunotoxin being evaluated. In four of the clinical trials more than 90% of the patients developed antibodies (Vitetta, E. S. et al., "Immunotoxins: Magic Bullets or Misguided Missiles? *Immunology Today* (1993) 14: 252–259).

Immunotoxin treatment needs to be given repeatedly in order to maximize tumor regression and eradication (Friedman, P. N. et al., "Antitumor Activity of the Single-Chain Immunotoxin BR96 sFv-PE40 Against Established Breast and Lung Xenografts" *J. Immunol.* (1993) 150: 3054–61; Skolnick, A. A., "First Immunotoxin Therapy for Many Common Solid Tumors Enters Phase I Clinical Trial" *JAMA* (1993) 270: 2280; and Wawrzynczak, E. J., "Systemic Immunotoxin Therapy of Cancer: Advances and Prospects" *Br. J. Cancer* (1991) 64: 624–630). When endogenous antibody formation occurs, the efficacy of immunotoxin treatment is substantially diminished or negated. This decreased efficacy is thought to result from the increased rate of clearance of the immunotoxin or from blocking of the receptor site or toxic activity site of the immunotoxin (Vitetta, E. S. et al., "Immunotoxins: Magic Bullets or Misguided Missiles? *Immunology Today* (1993) 14: 252–259; and Wawrzynczak, E. J. and Derbyshire, E. J., "Immunotoxins: the Power and the Glory" *Immunology Today* (1992) 13: 381–383).

Various approaches to overcome the problem of immunogenicity have been tried but without success. Immunosuppressive drugs such as cyclophosphamide, prednisone, azathioprine and cyclosporin A failed to prevent patients from developing endogenous antibody in the face of repeated administration of immunotoxin (Wawrzynczak, E. J., "Systemic Immunotoxin Therapy of Cancer: Advances and Prospects" *Br. J. Cancer* (1991) 64: 624–630). In experimental animals modification of a Pseudomonas exotoxin-derived immunotoxin with monomethoxy-polyethylene glycol (mPEG) diminished immunogenicity 5- to 10-fold, prolonged circulation time and preserved its antitumor effect (Wang, Q. C. et al., "Polyethylene Glycol-Modified Chimeric Toxin Composed of Transforming Growth Factor Alpha and Pseudomonas Exotoxin" *Cancer Research* (1993) 53: 4588–94). "Humanizing" the mouse-cell-derived monoclonal carrier antibody has been seen as a possible solution to the problem of immunogenicity (Skolnick, A. A., "First Immunotoxin Therapy for Many Common Solid Tumors Enters Phase I Clinical Trial" *JAMA* (1993) 270: 2280; and Winter, G and Harris, W. J., "Humanized Antibodies" *Immunol. Today* (1993) 14: 243–246). However, the recently accomplished replacement in mice of the mouse genes for antibody production with the human genes for antibody production may portend an unlimited supply and variety of fully human-compatible antibodies from mice (Green, L. L. et al., "Antigen-Specific Human Monoclonal Antibodies from Mice Engineered with Human Ig Heavy and Light Chain YACs" *Nature Genetics* (1994) 7: 13–21; and Lonberg, N. et al., "Antigen-Specific Human Antibodies from Mice Comprising Four Distinct Genetic Modifications" *Nature* (1994) 368: 856–859). Another effort to make immunotoxins less immunogenic used mouse/human antibody and a human-homolog RNase gene to create a novel "humanized" immunotoxin (Rybak, S. M. et al., "Humanization of Immunotoxins" *Proc. Natl. Acad. Sci.* (1992) 89: 3165–9). Because the current art has not solved the immunogenicity problem, a simple, safe and comfortable method to minimize or abolish the immunogenicity of immunotoxins in patients undergoing treatment with them is still needed.

Passive Immunization

Antibodies have been given to patients in order to achieve passive immunization. The antibodies may be obtained from human or animal donors who have recovered from an infectious disease or have been immunized. This antibody product can be either whole serum or fractionated concentrated immune (gamma) globulin, which is predominantly IgG. These antibodies can provide immediate protection to an individual deficient in such antibodies.

When antibodies are obtained from animals, the animal sera give rise to an immune response that leads to rapid clearance of the protective molecules from the circulation of the human recipient. Additionally, animal sera provide a risk of allergic reactions, particularly serum sickness or anaphylaxis.

With regard to human antibodies, special preparations of human immune globulin with a high titer of a specific antibody are available. These preparations are obtained by hyperimmunizing adult donors or by selecting plasma which was tested for a high specific antibody content. Although the side effects of human immune globulin are minimal, its intramuscular administration is painful and, although rare, anaphylactoid reactions have been described.

Passive immunization has been carried out for infectious and noninfectious diseases. As an example of a noninfectious disease treated with passive immunization, Rh-negative persons are at risk of developing anti-Rh antibodies when Rh-positive erythrocytes enter their circulation. For Rh-negative women, this occurs regularly during a pregnancy with an Rh-positive fetus. Development of anti-Rh antibodies by a mother threatens all subsequent Rh-positive fetuses with erythroblastosis fetalis and death. This scenario can be prevented by administration of Rh immune globulin (RhIG) to the Rh-negative mother. RhIG is produced by having Rh-negative volunteers (originally men or nuns, because these women did not plan to have children) be injected with Rh-positive red cells to induce antibodies. Then, these volunteers are plasmapheresed to harvest the immune plasma, which is then processed into RhIG.

By use of RhIG, erythroblastosis fetalis is avoided in future Rh-positive fetuses. Passive immunization with Rh immune globulin (RhIG) suppresses the mother's normal immune response to any Rh-positive fetal cells that may enter her circulation. Passive immunization with RhIG may also protect in a nonspecific manner, analogous to the 'blocking' effect of high-dose IgG in ameliorating autoimmune diseases such as idiopathic thrombocytopenic purpura (ITP). With ITP, the beneficial blocking effect is thought to derive from the ability of the infused antibody to bind to receptors in the spleen and to prevent that organ from destroying the platelets to which the host's own "autoimmune" antibodies have become adherent (Berkman, S. A., et al., . "Clinical Uses of Intravenous Immunoglobulins" *Ann. Int. Med.* (1990) 112: 278–292).

Passive immunization can be carried out in another context that relates to Rh isoimmunization. Rh isoimmunization may occur consequent to blood transfusion. Most transfusion reactions to Rh can be prevented by transfusing Rh-negative individuals with Rh-negative blood. Of the Rh antigens, the D antigen is a high-incidence, strongly immunogenic antigen, approximately 50 times more immunogenic than the other Rh antigens. Thus, when determining Rh status, transfusion blood is typed routinely for D, but+not for other Rh antigens. However, immunization to other Rh antigens may occur even when Rh-negative blood is given to Rh-negative patients, since donor blood is not routinely typed for the non-D Rh antigens. Additionally, immunization and antibody formation to Rh antigens can occur in Rh-negative individuals due to transfusion errors. RhIG can be used to passively immunize and protect individuals from such situations. RhIG addresses a spectrum of Rh antigens because of the way it is made, utilizing red cells that contain an array of Rh antigens. Thus, the resulting RhIG is directed to various Rh antigens, in addition to the Rh D antigen.

Accordingly, Rh immunization can now be suppressed almost entirely if high-titer anti-Rh immunoglobulin (RhIG), available under the tradename RHOGRAM® for (Ortho Pharmaceuticals, Raritan, N.J.), is administered within 72 hours of the time the potentially sensitizing dose of Rh-positive cells were given.

As is the case with RhIG administration to pregnant Rh-negative women, the protective mechanism by which RhIG administration prevents development of Rh antibodies in Rh-negative individuals is not clear. RhIG does not effectively block Rh antigen from immunoresponsive cells by competitive inhibition, since it is known that effective doses of RhIG do not cover all Rh antigen sites on the fetal (or wrongly transfused) erythrocytes. Intravascular hemolysis with rapid clearance of erythrocyte debris by the reticuloendothelial system is also unlikely. Rather, after the Rh-positive cells are removed from the circulation, the RhIG-induced erythrocyte hemolysis is believed to be extravascular, primarily by phagocytic cells in the spleen and, to a lesser extent, the lymph nodes. The most likely therapeutic mechanism resulting from RhIG administration is a negative modulation of the primary immune response. It is believed that antigen-antibody complexes become bound to lymph node and splenic cells that have Fc receptors. These lymph node and spleen cells presumably then stimulate suppressor T cell responses, which subsequently prevent antigen-induced B cell proliferation and antibody formation.

SUMMARY OF THE INVENTION

The present invention relates to a method of providing an adjunct to the therapeutic administration of one or more toxins. The toxin(s) may be a natural (or native) toxin such as an enzyme, a chimeric toxin, a recombinant toxin, an immunotoxin, or a combination of such toxins. The method comprises providing a human-compatible or human-derived antitoxin, where the antitoxin corresponds to the administered toxin(s). The antitoxin is intravenously injected into the patient who received the corresponding toxin(s). The chimeric toxins, recombinant toxins and immunotoxins may be prepared by chemical, biochemical, immunological or genetic engineering methods. Furthermore, the antitoxin for the invention may be produced as human or human-compatible monoclonal or polyclonal antibodies, chimeric antibodies, recombinant antibodies (e.g., single chain antibodies) or antigen-binding fragments of such antibodies. The antitoxin used should correspond to the therapeutically administered toxin and may contain varying proportions of several different antibodies directed against various epitopes on the toxin molecule. The purpose of providing antitoxin as an adjunct to the therapeutic administration of a toxin is to prevent or minimize any side-effects or complications that could arise from the injected toxin.

The present invention also comprises a method for treating a human patient who has a neuromuscular disorder, comprising administering a therapeutically effective amount of at least one botulinum toxin to the patient; providing a human-derived or human-compatible antitoxin that corresponds to the administered toxin; and intravenously injecting the antitoxin into the patient. For the method of treating, about 0.1 to 400 treatment units of botulinum toxin are administered during a treatment session. Generally, in this context, sufficient botulinum immunoglobulin is intravenously injected so as to neutralize about 10% to 90% of the injected toxin.

The present invention also comprises a composition for use as an adjunct to therapeutic toxin treatment of a human comprising a human-derived or human-compatible antitoxin that corresponds to the toxin.

DETAILED DESCRIPTION OF THE INVENTION

For the first time in the art a method is disclosed that prevents the development of antitoxin antibodies in patients treated with a toxin, such as a neurotoxin or immunotoxin, and prevents the unwanted side-effects, such as weakness of nontargeted muscles, due to the therapeutic administration of neurotoxin or nonspecific cytotoxicity due to the administration of immunotoxin. The method facilitates the therapeutic use of combinations of toxins and permits larger doses of the toxins to be used.

Typically, the method comprises use of intravenously injected, human-compatible or human-derived antitoxin antibodies. By "human-compatible" is intended antibodies that are not derived from a human source but which as provided have attendant features which allow them to avoid production of adverse effects, such as allergic reactions, when administered to a human. Accordingly, by use of human-compatible antitoxin antibody, patients can continue to obtain the therapeutic benefits of treatment with toxin(s), such as neurotoxin or immunotoxin therapy, upon subsequent treatment.

The method of the invention may be used in the administration of any natural toxin, chimeric toxin, recombinant toxin or immunotoxin, that is used as a therapeutic agent to treat a human disease or medical condition. Intravenous injection of antitoxin corresponding to the administered toxins at an appropriate dosage and time prevents toxin that escapes the intended site of action from stimulating production of antitoxin antibodies by the patient's immune system and from causing unwanted side-effects.

"Natural toxins" are molecules and macromolecules made by plants, animals and microbes that can poison other organisms. A "chimeric toxin" refers to poisonous molecules either created by joining parts derived from two or more natural toxins or created by joining all or part of a natural toxin with all or part of another large molecule, such as an antibody. For example, a chimeric toxin consisting of the "heavy" (ca. 100,000 MW) chain of botulinum toxin and the "light" (ca. 50,000 MW) chain of tetanus toxin was constructed and found to have six times the potency of native tetanus toxin (Weller, U. et al., "Cooperative Action of the Light Chain of Tetanus Toxin and the Heavy Chain of Botulinum Toxin Type A on the Transmitter Release of Mammalian Motor Endplates" *Neurosci. Letters* (1991) 122:

132–134). The combination of a targeting molecule and a toxic molecule or moiety (including radioisotopes and pharmaceuticals) into a novel macromolecule is termed an "immunotoxin." When immunotoxins are made by genetic engineering techniques that join the nucleic acid sequences of the carrier molecule and the toxin molecule, so that the targeting protein and toxin are covalently peptide-bonded together, the immunotoxin is sometimes referred to as a "recombinant toxin." Immunotoxins that act at the cell surface membrane have been termed "immunolysins."

In one embodiment, the method relates to the use of botulinum and tetanus neurotoxins, either singly or in combinations. The method also includes the use of neurotoxins produced by other sources, for example, the botulinum F-like toxin of *Clostridium baratii*, and the botulinum E-like toxin of *Clostridium butyricum*, and any other such toxins as may be discovered in the future. This method also includes the use of human botulinum or botulinum-like antitoxins, or other human-derived antitoxins, that may be produced in vitro as polyclonal or monoclonal antibodies or antigen-binding fragments of such antibodies from cell cultures. In another embodiment, the method relates to the use of chimeric toxins, recombinant toxins and immunotoxins, regardless of their original source of the toxin molecule or toxic agent.

Accordingly, the method relates to tetanus toxin, diphtheria toxin, Pseudomonas toxin, ricin and other biological toxins (plant, animal and microbial, regardless of chemical structure or nature) as therapeutic agents for use in human medicine. Examples of such toxins include, but are not limited to, spider venom toxins, sea snail toxins, snake venom toxins, scorpion toxins and microbial toxins such as saxitoxin, neosaxitoxin, tetrodotoxin, brevitoxins and ciguatoxin.

The method of preventing unwanted side-effects, such as production of endogenous antitoxin antibody, is based on the following three preferred principles:

1. Sufficient human-compatible antitoxin is intravenously injected to neutralize any corresponding toxin(s) that escapes from the treatment site, so that the toxin(s) does not stimulate the patient's immune system to produce endogenous antitoxin antibodies.
2. Intravenous injection facilitates that the antitoxin is dispersed throughout the extracellular fluid, where it mixes with and binds any escaped toxin(s), before the toxin diffuses or travels to nontargeted tissues.
3. In the case of neurotoxin therapy, the administration of antitoxin is advantageously delayed for a relevant period after therapeutic administration of the corresponding neurotoxin(s), so that the injected toxin(s) can bind to the intended site(s). In the case of immunotoxin therapy administered locally to umors, concomitant or earlier administration of antitoxin may be desirable to neutralize any immunotoxin that is not internalized in the target tissue.

As indicated above, the method facilitates toxin therapy in which combinations of toxins are used. Examples of such combination toxin therapy follow.

Use of Combinations of Botulinum and Tetanus Toxins Together with Their Corresponding Antitoxins Because the various botulinum and tetanus toxin light chains (proteases) have different substrates within the motoneuron cytosol, several two-fold and three-fold combinations are therapeutically beneficial. There are three groupings of two-fold combinations. First, any toxin listed in column (1) (Table 1, above) can be combined with any toxin listed in column (2); second, column (3) (i.e., type C toxin) can be combined with any toxin in column (1); and third, column (3) can be combined with any toxin in column (2). The beneficial three-fold combinations all contain type C toxin. Type C toxin can be combined with either type A or type E toxin and the resulting combination can then be combined with any of the toxins in column (1). These 10 combinations consist of ABC, ADC, AFC, AGC, A-tetanus-C, EBC, EDC, EFC, EGC, and C-E-tetanus.

Use of botulinum and tetanus toxin combinations enables a longer therapeutic effect to be achieved because several links in the secretory pathway of acetylcholine are severed simultaneously. In accord with the method herein disclosed, human-compatible antitoxin antibodies to botulinum toxins and tetanus toxin are used to prevent unwanted side-effects and complications of the therapeutic injection of combination of these toxins.

Use of a Combination of Botulinum Toxin and Cobra Toxin

Botulinum toxin causes muscle relaxation by acting pre-synaptically to prevent the release of acetylcholine. Cobra toxin also produces muscle relaxation, but does so by acting post-synaptically in a manner similar to d-tubocurarine. Consequently, combining botulinum toxin(s) with cobra toxin prolongs the duration of therapeutic muscle relaxation by blocking muscle contraction both pre-synaptically and post-synaptically.

In accord with the method herein disclosed, human-compatible antitoxic antibodies to botulinum toxin(s) and cobra toxin are used to prevent unwanted side-effects and complications of the therapeutic injection of this combination of toxin(s).

Use of Combination of Botulinum Toxin(s) and Cation Channel Blocking Agents

Certain omega-conotoxins produced by marine sea snails of the genus Conus target the P-type calcium channel, which is the predominant type of voltage-dependent calcium channel at the neuromuscular junction (Olivera, B. M. et al., "Conotoxins: Peptide Ligands for Receptors and Ion Channels" *Toxicon.* ( 1994) 32: 244; Uchitel, O. D. et al., "Characterization of Calcium Channels Involved in Transmitter Release at the Mammalian Neuromuscular Junction" *Toxicon.* (1994) 32: 240–41). An increase in intracellular calcium concentration counteracts the action of botulinum toxin (Cull-Candy, S. G. et al., "Effects of Botulinum Toxin on Neuromuscular Transmission in the Rat" *J. Physiol.* (1976) 260: 177–203).

Saxitoxin is produced by sea-dwelling dinoflagellates of the genus Gonyaulax. Tetrodotoxin is produced by the Japanese puffer fish and some species of newts and frogs. Both saxitoxin or tetrodotoxin are sodium channel blocking agents that cause muscle relaxation and paralysis by preventing the nerve impulse from travelling from the spinal cord along the axon to the neuromuscular junction (Ritchie, J. M., Greene, N. M. in Gilman, A. G., Rall, T. W., Nies, A. S., Taylor, P., eds. *The Pharmacologic Basis of Therapeutics, eighth edition.* Pergamon Press, New York 1990 at p. 322).

Combining *Clostridium botulinum* toxin(s) with a cation-channel blocking agents prolongs the duration of therapeutic muscle paralysis by blocking two or more separate steps in the nerve signalling pathway of muscle contraction. In accord with the method herein disclosed, human-compatible antitoxic antibodies to botulinum toxin(s) and to cation-channel toxins are used to prevent the unwanted side-effects and complications of the therapeutic injection of this combination of toxins. Combining *Clostridium perfringens* and Clostridium histolyticumCollagenages to Treat Conditions with Excess Connective Tissue Formation The collagenases produced by *Clostridium perfringens* are known as kappa toxins (McDonel, J. L., "*Clostridium perfringens* toxins ((type A,B,C,D,E))" *Pharmac. Ther.* (1986) 10: 617–655). *Clostridium perfringens* type A produces an 80-kD collagenase (Kameyama, S. and Akama, K., "Purification and Some Properties of Kappa Toxin of *Clostridium perfringens*" *Japan J. Med. Sci. Biol.* (1971) 24: 9–23), while type C strains produce a 120-kD collagenase (Matsushita, O. et al., "Purification and Characterization of a *Clostridium perfringens* 120-kilodalton Collagenase and Nucleotide Sequence of the Corresponding Gene" *J. Bacteriol.* (1994) 76: 149–56).

Beta toxin was the name originally given to the collagenase activity produced by *C. histolyticum* (Smith, L. D. S. *The Pathogenic Anaerobic Bacteria*, second edition. CC Thomas, Springfield, Ill. 1975 at pp. 284–86), which was later shown to consist of seven distinct collagenase enzymes (Mookhtiar, K. A. and Van Wart, H. E., "*Clostridium histolyticum* Collagenases: a New Look at Some Old Enzymes" Matrix (1992) Suppl. 1: 116–26). Collagenases can be used to treat medical conditions in which there is excess or misplaced connective tissue formation, such as rheumatoid arthritis or keloid formation. Combining collagenases that digest the collagen molecule at different substrate sites results in better removal of the excess or unwanted connective tissue.

Keloids are cosmetically objectionable proliferations of scar tissue (collagen) that occur in response to minor skin trauma. Keloid formation is genetically determined and is more common in persons of African descent. Rheumatoid arthritis is an inflammatory condition in which joints become enlarged, deformed and immobilized by excess connective (collagen) tissue proliferation. In both these conditions the excess collagen can be decreased or removed by injection of mixtures of clostridial collagenases by those of ordinary skill in the art.

In accord with the method herein disclosed, human-compatible antitoxic antibodies to bacterial collagenase toxins are made by standard methods. These antitoxins are then used to prevent unwanted side-effects and complications from therapeutic injection of these combinations of bacterial collagenase toxins.

As indicated above, the method may be used in the administration of chimeric toxins or immunotoxins. Examples of such use follows.

Use of a chimeric Toxin to Provide Permanent Relief of Muscle spasm

A chimeric toxin is made with known techniques to join the active fragment of *Pseudomonas aeruginosa* exotoxin A with the nerve cell receptor-binding ("heavy") chain of botulinum neurotoxin. The active portion of Pseudomonas exotoxin is a ribosomal poison that causes cell death by ADP-ribosylation of elongation factor 2. The heavy chain of botulinum toxin delivers the chimeric toxin presynaptically to the neuromuscular junctions of the overactive muscles into which the chimeric toxin has been injected. As happens in natural botulism poisoning, the chimeric toxin (or an active portion of it) is taken inside the cell cytoplasm by endocytosis. Once free in the cytoplasm, the Pseudomonas exotoxin portion of the molecule is carried by retrograde axoplasmic flow to the spinal cord and main cell cytosol, where it kills the overactive nerve cell by blocking protein synthesis. In this way the patient receives permanent relief from the pathological muscle overactivity or spasm.

In accord with the method herein disclosed, human-compatible antitoxin antibodies to both toxic components of the chimeric toxin are used to prevent unwanted side-effects and complications from therapeutic injection of this chimetic toxin. In this example antibodies against Pseudomonas exotoxin are especially needed to capture and inactivate any exotoxin that may separate from the chimeric molecule before the free exotoxin could injure other tissues.

Chimeric Toxins and Immunotoxins that Use Human Ribonuclease as the Toxic Substance A new class of therapeutic agents has recently been developed based on the behavior of the enzyme ribonuclease (RNase). When RNase gains entry into a cell, it degrades that cell's ribonucleic acid (RNA)-containing structures, thereby causing the cell to die. By use of biochemical and genetic engineering techniques, human RNase molecules have been coupled to antibodies with desired target specificity (e.g., tumor cells). Although chimeric immunotoxins that use human RNase are less immunogenic than immunotoxins made with plant or bacterial toxins, the problem of new antigenic epitopes arising from the fusion of otherwise unrelated molecules has not been solved (Youle, R. J. et al., "Cytotoxic Ribonucleases and Chimeras in Cancer Therapy" *Critical Reviews Therapeutic Drug Carrier Systems* (1993) 10: 1–28; and Vitetta, E. S. et al., "Immunotoxins: Magic Bullets or Misguided Missiles? *Immunology Today* (1993) 14: 252–259).

Human-compatible antitoxin antibodies or antibody fragments are made by standard techniques and used in accord with the methods disclosed in this invention to prevent unwanted side-effects and complications from the therapeutic injection of these RNase-containing chimeric toxins.

Improved Treatment of Solid Tumors (e.g., Liver, Lung, Brain) with Immunotoxins and Anti-Immunotoxins Use of immunotoxins in the treatment of hematological malignancies and of disorders mediated by leukocytes has been more successful than their use in solid tumors has been. This disparity reflects the difficulty in ensuring that at least one immunotoxin molecule reaches each malignant cell in the solid tumor. This difficulty results in part from the large number of immunotoxin-specific receptors on each tumor cell and from the disproportion between the size of the tumor mass and its blood supply. These anatomical considerations enable the tumor cells closest to the capillary bed to absorb all immunotoxin molecules as they diffuse out of the vasculature, thereby allowing no immunotoxin molecules to reach more distal tumor cells.

One approach to overcoming this difficulty is to give repeated infusions of immunotoxins, thereby killing the tumor in increments. When the infusion is given intravenously into the systemic circulation, the immunotoxin disperses widely and provokes an immune response. Once the patient develops antibody against the immunotoxin, it renders further treatment with immunotoxin less effective or ineffective by shortening its half-life and by neutralizing the immunotoxin's toxic activity.

In a recent review of completed or ongoing clinical trials with immunotoxins, it was noted that "optimal regimens for administration of immunotoxins have not yet been devised. The half-lives in trials to date have generally been shorter than would be predicted to induce an optimal therapeutic index" (Vitetta, E. S. et al., "Immunotoxins: Magic Bullets or Misguided Missiles?" *Immunology Today* (1993) 14: 252–259). The maximum tolerated dose of a variety of immunotoxins studied ranged from 0.05–3.3 mg/kg (n=11), while their half-lives ranged from 0.1–8.3 hours (n=8). Accordingly, the amount of antitoxin to provide a given patient with a particular tumor cannot be precisely specified in advance, but depends on the characteristics of the tumor and of the particular immunotoxin being used.

In patients with cancer, there is variation in the histologic cell type of the tumor, in the size of the tumor, in the location of the tumor, in the density of tumor-specific antigens on the surface of the tumor, and in the binding avidity of the immunotoxin to the surface antigens of the tumor. Hence, there is variation in the overall response to treatment with the immunotoxin, as is known and appreciated by those of ordinary skill in the art. For this reason, the amount of immunotoxin which is injected into a particular patient at a particular time is a clinical decision to be determined by the attending physician, based on information known to those of ordinary skill in the art.

Nonetheless, the therapeutic principles underlying the use of antitoxin as a therapeutic adjunct to immunotoxin administration are the same as those underlying therapeutic injection of a neurotoxin(s), viz., to neutralize toxin(s) not bound by the tumor before they can injure normal tissue and before they can stimulate an endogenous antibody response. A sufficient amount of antitoxin should be given to accomplish these purposes.

Treatment of solid tumors with immunotoxins can be improved by the following novel method. The immunotoxin is delivered directly to the tumor by means of an intraarterial catheter whose tip is placed as closely as possible to the origin of the neovasculature that supplies the tumor. An appropriate amount of immunotoxin is injected through the catheter, in this way delivering the highest concentration of immunotoxin to the tumor. However, because of anatomical considerations, not all injected immunotoxin will be taken up and bound by the tumor. In order to remove the non-tumor-binding immunotoxin that has passed by the tumor mass and entered the systemic circulation before the non-binding immunotoxin can stimulate endogenous antibody production, an appropriate amount of human-compatible antitoxin is administered intravenously almost immediately, i.e., within 1–120 minutes of the therapeutic immunotoxin injection. The appropriate amount of antitoxin to administer can be determined by measuring the amount of unbound immunotoxin in the patient's bloodstream, as for instance, by means of an ELISA assay. However, if several solid tumor masses need to be injected as part of a single catheter immunotoxin treatment session, then infusion of the corresponding human-compatible antitoxin can be delayed until the treatment session is finished.

As a further extension of the method, if the immunotoxin is given by catheter and much of it is known to bind to the tumor, an appropriate amount of antitoxin may be given a short time (5–120 minutes) before the immunotoxin is given. In this way, the antitoxin will have reached an equilibrium, low-level concentration in the circulation when the immunotoxin is injected, so that the antitoxin will be present to neutralize any immunotoxin that fails to bind to the tumor. However, by administering only enough antitoxin to neutralize the unbound immunotoxin, the antitoxin will not be at so high a level that it blocks the injected immunotoxin from binding to the tumor.

The liver represents an advantageous organ for the application of this method because it is the site of primary hepatocellular carcinoma (HCC) and of metastases from many tumors, e.g. bowel, breast, lung. When intrahepatic artery injection of an immunotoxin treatment for HCC was tried, no corresponding antitoxin was used, and 43% (10/23) of patients developed antibodies against the immunotoxin within 2–4 weeks of starting therapy (Zeng, Z. C. et al., "Radioimmunotherapy for Unresectable Hepatocellular Carcinoma Using $I^{131}$-Hepama-1 mAb: Preliminary Results" *J. Cancer Res. Clin. Oncol.* (1993) 119: 257–9). In the novel method herein disclosed, a catheter is advanced into the hepatic artery as closely as possible to the origin of the neovasculature of the tumor or tumors (if more than one metastasis is present) before injecting the immunotoxin. After the immunotoxin has been injected, infusion of the corresponding human-compatible antitoxin is made by peripheral vein almost immediately in order to bind any immunotoxin that has not attached to the tumor. Alternatively, if clinical circumstances and immunotoxin characteristics make it feasible, the antitoxin can be given before the immunotoxin is injected. Treatment is repeated as many times as necessary to eradicate the tumor.

The lungs are readily catheterized through the pulmonary arteries. The catheter tip is placed as closely as possible to the tumor mass(es), and the immunotoxin is injected. Corresponding human-compatible antitoxin is infused almost immediately through a peripheral vein. Alternatively, if clinical circumstances and immunotoxin characteristics make it feasible, the antitoxin can be given before the immunotoxin is injected. Treatment is repeated as many times as necessary to eradicate the tumor.

Some brain tumors are resistant to radiation therapy and chemotherapy and are located in surgically inaccessible sites. For these tumors a catheter is placed in the internal carotid or vertebral artery and advanced as closely as possible to the origin of the tumor's blood supply. The immunotoxin is injected, followed almost immediately by infusion of the corresponding antitoxin by peripheral vein. Alternatively, if clinical circumstances and immunotoxin characteristics make it feasible, the antitoxin can be given before the immunotoxin is injected. Treatment is repeated as many times as necessary to eradicate the tumor.

The following examples further illustrate the invention.

EXAMPLES

Example 1

Use of Botulinum Toxin and Botulism Immune Globulin

In one embodiment, the invention includes use of human-compatible botulinum antitoxin antibodies injected intravenously to preclude the effect of any toxin that leaks or diffuses away from the site of injection. Use of human-derived botulinum antitoxin antibodies avoids the problems of allergic sensitization and antibody induction that occur with the horse-derived antitoxin.

Botulism Immune Globulin (BIG):

A new preparation of human-derived botulinum antitoxin recently came into existence as an Investigational New Drug (BB-IND-4283); this antitoxin is called Botulism Immune Globulin (BIG). Unlike the BIG made earlier by the U.S. Army, this new preparation of BIG was made in complete compliance with the requirements for licensure of biological products established by the U.S. Food and Drug Administration (FDA). Specifically, for human-derived immune globulins, the FDA requires that the source plasma be collected in an FDA-licensed plasmapheresis facility and that the source plasma be fractionated into immune globulin in an FDA-licensed facility that meets the standards of Good Manufacturing Practice (GMP). BIG contains IgG antibodies that can neutralize botulinum toxin types A–E; these antibodies were obtained by plasmapheresis of botulinum toxoid-immunized volunteers. (Arnon, S. S., "Clinical Trial of Botulism Immune Globulin" pp. 485–90 in DasGupta, B.

R., ed. *Botulinum and Tetanus Neurotoxins: Neurotransmission and Biomedical Aspects,* Plenum Press, NY (1993))

Botulism Immune Globulin Intravenous (Human) is a sterile lyophilized powder of immunoglobulin G (IgG), stabilized with 5% sucrose and 1% Albumin (Human). It contains no preservative. The purified immunoglobulin was derived from pooled adult human plasma from persons immunized with pentavalent (ABCDE) botulinum toxoid, who were selected for their high titers of neutralizing antibody against botulinum neurotoxin types A,B,C,D, and E. All donors were tested and found negative for antibodies against the Human Immunodeficiency Virus (HIV), the hepatitis B and C viruses, and the HTLV-I virus. In addition, each individual unit of donated immune plasma was tested and found negative for antibody against the HIV and hepatitis B viruses.

The pooled plasma was fractionated by ethanol precipitation of the proteins according to Cohn Methods 6 and 9, modified to yield a product suitable for intravenous administration. Cohn methods 6 and 9 are known to be capable of inactivating the AIDS (HIV) virus. When reconstituted with Sterile Water for Injection, USP, each milliliter contains 50 ±10 mg of immunoglobulin, primarily IgG, and trace amounts of IgA and IgM; 50 mg of sucrose; 10 mg of Albumin (Human). The reconstituted solution appeared colorless and translucent.

Toxin Treatment:

The method of the invention includes the use of botulinum toxin types for which human-derived antitoxin antibody presently exists (A-E), as well as for human-derived antitoxin antibody to types F and G, and for human-derived antitoxin antibody for any botulinum toxin types that may be discovered in the future.

The treatment dose of botulinum toxin which is injected into a patient varies with the size and location of the muscle(s) to be treated; the dose of BIG which is injected intravenously varies accordingly. For adults, the therapeutic dose of botulinum toxin which is injected per session ranges from as little as about 0.1 treatment unit (t.u.) of botulinum toxin (e.g., for cosmetic eye wrinkle use), and in certain circumstances, to as much as about 400 t.u. (e.g., in a very large dystonia patient, such as a professional football player or sumo wrestler). The desired amount of BIG that is injected is an amount sufficient to neutralize about 10% to 90% of the injected toxin. The amount of toxin neutralized can vary depending on such criteria as the disease and age, size and the like of the patient treated so that the amount may not be the same for every disease or every patient; the optimal ratio is determined based on clinical experience possessed by those of ordinary skill in the art. The optimal ratio depends on the proportion of injected toxin that leaks from the injected muscle(s); this proportion is not the same for all muscles because of the vastly different sizes of muscles injected in different diseases, as is appreciated and known to those of ordinary skill in the art. However, it is understood that anywhere from 10% to 90% of injected toxin may be able to leak from the injection site, and hence, enough BIG is provided to neutralize this amount of toxin. Additionally, BIG which is injected intravenously distributes itself over the entire volume of extracellular fluid (i.e., the interstitial and intravascular fluid compartments). It is recognized that in some clinical situations a locally higher concentration of BIG is called for (e.g., when large amounts of toxin are injected into dystonic neck muscles); this is taken into account when determining the amount of BIG which is provided.

BIG is calibrated in International Units (IU), whereas botulinum toxin is calibrated in treatment units (t.u.). The relation between the two is that, by definition, 1 International Unit (IU) of BIG neutralizes 10,000 treatment units (t.u.) of type A botulinum toxin. Therefore, the amount of BIG needed by a patient in a single intravenous injection to accompany an intramuscular treatment with botulinum toxin is generally be between $1\times10^6$ to $3.6\times10^{-2}$ International Units of BIG.

Preferably, the desired amount of BIG is injected intravenously between about 2 and 24 hours after the intramuscular injection of botulinum toxin. An initial 4-hour delay is preferred, so as to provide the toxin with sufficient time to bind at the intended sites in the treated muscle. The time range of post-toxin injection of BIG is to permit necessary clinical latitude appropriate to individual patient circumstances, as the optimal time interval can vary depending on the patients and the disease conditions. However, if BIG is not administered within this 2–24 hour time interval, yet still in accordance with the invention, BIG can be given up to 72 hours to prevent the induction of antitoxin antibodies. Late administration of BIG may not fully prevent the weakening of muscles adjacent to the toxin injection site, depending on the local anatomy and the amount of toxin which is injected.

Preferably, only a single intravenous injection of BIG is needed at each treatment session because the half-life of human immunoglobulin in humans is approximately 30 days. (Ochs, H. D., et al., "Survival of IgG Subclasses Following Administration of Intravenous Gamma-Globulin in Patients with Primary Immunodeficiency Diseases," pp. 77–85 in Morell, A., Nydegger, U. E., eds., *Clinical Use of Immunoglobulins,* Academic Press, London (1986); Mankarious, S., et al., "The Half-Lives of IgG Subclasses and Specific Antibodies in Patients with Primary Immunodeficiency Who Are Receiving Intravenously Administered Immunoglobulin" *J. Lab. Clin. Med.* (1988) 112: 634–40) The half-life of BIG correlates with a further consideration when establishing the dosage of BIG. The effects of intramuscular injected toxin typically begin to wear off about 3 months after treatment, whereupon retreatment typically becomes necessary. Consequently, at the time of toxin retreatment, it is important that before retreatment, the BIG level in the circulation has declined to sub-clinical significance; otherwise, residual BIG serves to partially block the effect of the next toxin treatment. For this reason, and as readily appreciated by those of ordinary skill in the art, it is important to give the patient only the amount of BIG indicated for the specific amount of toxin administered at each treatment session.

There is variation among patients in their duration of illness before coming to treatment, in the severity of their illnesses, in the size of their muscle(s) needing toxin injection, in their individual sensitivity to equivalent amounts of injected toxin, and hence, in their overall response to treatment with toxin, as is known and appreciated by those of ordinary skill in the art. For this reason, the amount of toxin which is injected into a particular patient with a particular problem at a particular time is a clinical decision to be determined by the attending physician., based on information known to those of ordinary skill in the art. Since the amount of toxin that either binds at or leaks from the treatment site varies with the clinical circumstances, some patients treated with both toxin and BIG have a diminished response to the injected toxin, because some portion of the toxin is neutralizable at the time the BIG is injected. Diminution in the effect of injected toxin may be overcome by increasing the dose of toxin (or decreasing the dose of BIG) during treatment sessions or by repeating the toxin and BIG injections at shorter intervals, as appreciated by those of ordinary skill in the art.

Example 2

Use of *Clostridium perfringens* Kappa Toxin(s) and Corresponding Antitoxin

Collagen is the major structural protein in the body, and a main component of connective and fibrous tissue. Accordingly, collagen constitutes approximately 25% of all body protein.

The obligate anaerobic bacterium *Clostridium perfringens* produces numerous "virulence factors," some of which are lethal to mammals and therefore referred to as toxins (Smith, L. D. S., "Virulence factors of *Clostridium perfringens*." *Rev. Infect. Dis.* (1979) 1: 254–60; McDonel, J. L., "*Clostridium perfringens* Toxins (Type A,B,C,D,E)." *Pharmac. Ther.* (1986) 10: 617–55). One of these "virulence factors," the kappa toxin, is a protein molecule and enzyme that digests collagen (a "collagenase").

The collagenase (kappa toxin) produced by *C. perfringens* is used to treat patients with excessive fibrous connective ("scar") tissue. Because collagen is a component of many body tissues, it is particularly important that injected collagenase ("kappa toxin") not be able to diffuse away from the site of therapeutic administration and affect adjacent tissues. Further, therapeutic use of kappa toxin(s) induces the patient's body to produce antitoxin. This antitoxin corresponding to the kappa toxin(s) decreases the treatment efficacy of the kappa toxin. To overcome the problems of toxin diffusion and induction of antitoxin antibodies, a method in accordance with the invention is carried out for the treatment of several conditions. Treating patients undergoing kappa toxin therapy with the provision of an appropriate antitoxic antibody directed against kappa toxin(s) enables these therapeutic considerations to be met.

For example, a tendency to produce excessive connective ("scar") tissue in response to traumatic injury is particularly prevalent among some persons of African descent. This tendency to produce excessive collagen is genetically determined and is present throughout an effected person's life. This excessive formation of scar tissue occurs in response to otherwise trivial injury and may become quite cosmetically objectionable to the patient. On the skin these abnormal accumulations of fibrous tissue are termed "keloids"; typically they are large, raised, unsightly lesions.

Kappa toxin(s) is used to treat the formation of excessive connective tissue in effected individuals. These methods eliminate connective tissue accumulations or reduce their size, and are generally repeated over the life of the patient. Due to repeated exposure to the toxin, antibodies to the toxin develop in some patients. These antibodies reduce the efficacy of the treatment. Hence it is important that a patient not develop antibodies against kappa toxin(s) when the toxin is used for this purpose.

Also, certain chronic diseases are characterized by proliferation of connective tissue which then becomes injurious to the patient. Rheumatoid arthritis is such a disease, whereby chronic inflammation of an effected joint capsule leads to excessive connective tissue formation, and consequently, to enlarged, immobile joints. Kappa toxin(s) is used to treat this connective tissue formation. Because rheumatoid arthritis is a chronic disease, these patients also require repeated treatments with kappa toxin(s) to reduce or eliminate the unwanted connective tissue proliferation. Due to repeated exposure to kappa toxin(s), the patients can develop antibodies to the toxin(s). These antibodies reduce the efficacy of the treatment. Because this treatment generally must continue for the duration of the disease (i.e., the patient's remaining lifetime), it is important that the patient not develop antibodies against kappa toxin(s) when it is used for this therapeutic purpose.

Accordingly, human-compatible, human-derived antibodies to kappa toxin(s) are obtained by injecting volunteers with kappa toxoid, made by treating kappa toxin(s) with formalin in accord with standard procedures for preparing toxoids of protein molecules. Thereafter, appropriate therapeutic administration, in accordance with parameters appreciated by those of ordinary skill in the art, of the anti-kappa-toxin antibody protects the patient against the unwanted development of endogenous antibody, antibody that would result in insensitivity to further treatment with kappa toxin(s). Also, provision of anti-kappa-toxin antibody protects against diffusion ("leakage") of the collagenase from its injection site other tissues.

Example 3

New Checks Use of Color Meurotoxin and Corresponding Antitoxin

Cobra neurotoxin is used in the treatment of spasmodic dystonias. Use of cobra neurotoxin in this manner is a further example in which exogenous antitoxin antibodies are used to protect patients from becoming refractory to therapeutically injected toxin, as a consequence of the patient developing antibodies against the toxin. Use of cobra neurotoxin offers dystonia patients a additional means, in addition to use of botulinum toxin, for treating their disease.

Cobra neurotoxin is a small (MW 6949 daltons) basic protein that, like botulinum toxin, produces flaccid paralysis by its action at the neuromuscular junction. Unlike botulinum toxin which acts pre-synaptically, however, cobra neurotoxin acts post-synaptically in a manner pharmacologically similar to d-tubocurarine (Lee, C. Y., "Mode of Action of Cobra Venom and its Purified Toxins" in Simpson, L. L., ed., *Neuropoisons: their pathophysiological actions*, pp. 21–70 (Plenum Press, NY, 1971)).

Cobra neurotoxin is a much smaller molecule than crystalline botulinum toxin. Consequently, it diffuses away from the injection site more readily than botulinum toxin. Since it is a foreign protein, cobra neurotoxin that escapes the injection site can, both, stimulate an unwanted antibody response by the patient, and weaken muscles adjacent to the treated muscles. For these reasons it is particularly advantageous that patients treated with cobra neurotoxin receive antitoxin antibodies to prevent the occurrence of these unwanted complications of treatment.

Human-compatible antibodies to cobra neurotoxin (cobra antitoxin) are produced according to known methodologies. The cobra antitoxin is administered in an appropriate regimen, according to parameters appreciated by those of ordinary skill in the art, and prevents development of endogenous antibodies by the patient. Were the patient to have developed antibodies to the cobra toxin, treatment efficacy would be diminished. By use of the human-compatible antibodies, continued efficacious treatment with the toxin occurs.

All publications and patent applications cited in this specification are incorporated by reference herein, as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention, that certain changes and modifications may be made thereto without departing from the spirit or scope of the appended claims.

What is claimed is:

1. An improved method of providing toxin therapy to a human patient by administering an effective non-lethal dose of a toxin to a treatment site in the patient wherein the improvement comprises administering intravenously to the patient a human-derived or human-compatible antitoxin that binds specifically to the toxin in an amount and at a time sufficient to prevent toxin that fails to bind to said site from stimulating the patient's immune system to produce endogenous antitoxin antibodies.

2. The method of claim 1 wherein the administered toxin is a natural toxin, a chimeric toxin, a recombinant toxin, or an immunotoxin.

3. The method of claim 2 wherein the toxin is *Clostridium baratii* type F-like toxin.

4. The method of claim 2 wherein the toxin is *Clostridium butyricum* type E-like toxin.

5. The method of claim 1 wherein the administered toxin is botulinum toxin.

6. The method of claim 5 wherein the antitoxin is human botulism immune globulin.

7. The method of claim 5 wherein the antitoxin comprises antibodies to botulinum toxin type A, B, C, D or E.

8. The method of claim 5 wherein the antitoxin comprises antibodies to botulinum toxin type F or G.

9. The method of claim 1 wherein the administered toxin is tetanus toxin.

10. The method of claim 1 wherein the administered toxin is cobra neurotoxin.

11. The method of claim 1 wherein the site is muscle tissue, the toxin is a neurotoxin that temporarily paralyzes the muscle tissue, the administration is to the muscle tissue and the step of intravenously administering the antitoxin occurs between about two hours and seventy-two hours after the patient has received the toxin.

12. The method of claim 1 wherein the administered toxin is *Clostridium perfringens* kappa toxin.

13. The method of claim 1 wherein the toxin is *Clostridium histolyticum* beta toxin.

14. The method of claim 1 wherein the human-derived antitoxin is monoclonal or polyclonal.

15. The method of claim 1 wherein the antitoxin is a monoclonal antibody, a polyclonal antibody, a chimeric antibody, a recombinant antibody or an antigen-binding fragment of an antibody.

16. An improved method for causing temporary paralysis of muscle tissue in a human patient for a therapeutic purpose by administering an effective non-lethal dose of a neurotoxin to the muscle tissue wherein the improvement comprises intravenously administering an antitoxin that binds specifically to said neurotoxin to the patient in an amount and at a time sufficient to prevent neurotoxin that may escape from the tissue from stimulating the patient's immune system to produce endogenous antitoxin antibodies.

* * * * *

UNITED STATES PATENT AND TRADEMARK OFFICE
CERTIFICATE OF CORRECTION

PATENT NO. : 5,562,907

DATED : Oct. 8, 1996

INVENTOR(S) : Stephen S. Arnon

It is certified that error appears in the above-indentified patent and that said Letters Patent is hereby corrected as shown below:

On page 1:

In Attorney, Agent or Firm:

Insert -- Thomas E. Ciotti, -- before "Morrison & Foerster".
Insert -- LLP -- after "Morrison & Foerster".

In 56, References Cited U.S. PATENT DOCUMENTS:

Delete "5,053,005 10/1991 Bovodic" and insert -- 5,053,005 10/1991 Borodic --.
Delete "5,183,462 2/1993 Bovodic" and insert -- 5,183,462 10/1991 Borodic --.

In 56, References cited OTHER PUBLICATIONS:

Delete "Arnon (1993) In "Botolinum and Tetanus Neurotoxeus: Neurotrossnussion and Biomedical Aspects" (Das Gypto, ed.) Plenum Press, N.Y., pp 477-482, title & publ. pages."
and insert -- Arnon (1993) In *"Botulinum and Tetanus Neurotoxins: Neurotransmission and Biomedical Aspects"* (Das Gupta, ed.) Plenum Press, N.Y., pp. 477-482, title & publ. pages. --.

Delete "Franz et al (1993) In "Botolinum and Tetanus Neurotoxes: Neurotrossnussion and Biomedical Aspects" (Das Gupta, ed.) Plenum Press, N.Y., pp 473-476, title & publ. pages."
and insert -- Franz et al. (1993) In *"Botulinum and Tetanus Neurotoxins: Neurotransmission and Biomedical Aspects"* (Das Gupta, ed.) Plenum Press, N.Y., pp. 473-472, title & publ. pages. --.

UNITED STATES PATENT AND TRADEMARK OFFICE
CERTIFICATE OF CORRECTION

PATENT NO. : 5,562,907
DATED : Oct. 8, 1996
INVENTOR(S) : Stephen S. Arnon

It is certified that error appears in the above-indentified patent and that said Letters Patent is hereby corrected as shown below:

On page 1:

Delete "Hall et al., "Isolation of an Organism Resembling *Clostridium baratt*Which Produces Type F Botulinal Toxin from an Infant with Botulism" J. Clin. Microbiol. (1985) 21(4):654-655."

and insert -- Hall et al., "Isolation of an Organism Resembling *Clostridium barati* Which Produces Type F Botulinal Toxin from an Infant with Botulism" J. Clin. Microbiol. (1985) 21(4):654-655. --.

Delete "Hatheway, "Bacteriology and Pathology of Neurotoigenic Clostridia" *Botulinum and Tetanus Neurotoxins: Neurotransmission and Biomedical Aspects*, DasGupta, ed., Plenum Press, New York, 1993, pp. 491-502."

and insert -- Hatheway (1993) In *"Botulinum and Tetanus Neurotoxins: Neurotransmission and Biomedical Aspects"* (Das Gupta, ed.) Plenum Press, N.Y., pp. 491-502. --.

Delete "Suen et al., "*Clostridium argentinese*, sp. nov: A Genetically Homogenous Group Composed of All Strains of *Clostridium botulinum* Toxin Type G and Some Nontoxigenic Strains Previously Identified as *Clostridium subterminaleor Clostridium hastiforme*" *Int. J. System. Bacteriol.* (1988) 38(4):375-381."

and insert -- Suen et al., "*Clostridium argentinese*, sp. nov: A Genetically Homogenous Group Composed of All Strains of *Clostridium botulinum* Toxin Type G and Some Nontoxigenic Strains Previously Identified as *Clostridium subterminale or Clostridium hastiforme*" *Int. J. System. Bacteriol.* (1988) 38(4):375-381. --.

UNITED STATES PATENT AND TRADEMARK OFFICE
CERTIFICATE OF CORRECTION

PATENT NO. : 5,562,907

DATED : Oct. 8, 1996

INVENTOR(S) : Stephen S. Arnon

It is certified that error appears in the above-indentified patent and that said Letters Patent is hereby corrected as shown below:

On page 1:

Delete "Koening et al., "Clinical and Laboratory Observations on Type E Botulism in Man" *Medicine* (1964) 43:517-545."

and insert -- Koenig et al., "Clinical and Laboratory Observations on Type E Botulism in Man" *Medicine* (1964) 43:517-545 --.

On page 2:

Delete "Leary, "Gains Reported in Transferring Genetic Material to Mice" *New Youk Times* (Mar. 30, 1993) p. B8."

and insert -- Leary, "Gains Reported in Transferring Genetic Material to Mice" *New York Times* (Mar. 30, 1993) p. B8. --.

Delete "Mariani et al., "A New Enzymatic Method to Obtain High-Yield F(ab)$_2$ Suitable for Clinical Use from Mouse IgG1" *Mol. Immunol.* (1991) 28(1/2):69-77."

and insert -- Mariani et al., "A New Enzymatic Method to Obtain High-Yield F(ab)$_2$ Suitable for Clinical Use from Mouse IgG1" *Mol. Immunol.* (1991) 28(1/2):69-77. --.

UNITED STATES PATENT AND TRADEMARK OFFICE
CERTIFICATE OF CORRECTION

PATENT NO. : 5,562,907
DATED : Oct. 8, 1996
INVENTOR(S) : Stephen S. Arnon

It is certified that error appears in the above-indentified patent and that said Letters Patent is hereby corrected as shown below:

On page 2:

Delete "Mittendorf et al., "RH$_0$(D) Immunoglobulin (RhoGAM): How It Came into Being" *Obstetrics and Gynecology* (1991) 77(2):301-303."

and insert -- Mittendorf et al., "Rh$_0$(D) Immunoglobulin (RhoGAM): How It Came into Being" *Obstetrics and Gynecology* (1991) 77(2):301-303. --.

Delete "Lee, "Mode of Action of Cobra Venom and its Purified Toxins" Neuropoisons: Their pathophysiological actions Simpson, ed., Plenum Press, New York, 1971, pp. 21-70."

and insert -- Lee, "Mode of Action of Cobra Venom and its Purified Toxins" *Neuropoisons: Their pathophysiological actions* (Simpson, ed.) Plenum Press, New York, 1971, pp. 21-70. --.

Delete "Carruthers et al., "Treatment of Glabellar Frown Lines with C. botulinum -A Exotoxin" *J. Dermatol. Surg. Oncol.* (1992) 18:17-21."

and insert -- Carruthers et al., "Treatment of Glabellar Frown Lines with C. botulinum-A Exotoxin" *J. Dermatol. Surg. Oncol.* (1992) 18:17-21. --.

UNITED STATES PATENT AND TRADEMARK OFFICE
CERTIFICATE OF CORRECTION

PATENT NO. : 5,562,907

DATED : Oct. 8, 1996

INVENTOR(S) : Stephen S. Arnon

It is certified that error appears in the above-indentified patent and that said Letters Patent is hereby corrected as shown below:

<u>In the Specification:</u>

Column 3, line 45, delete "-608) Jankovic and Schwartz" and insert-- -608). Jankovic and Schwartz".

Column 8, line 27, delete "in vitro" and insert -- *in vivo* --.

Column 11, line 6, delete "D, but+not" and insert -- D, but not --.

Column 11, line 20, delete "RHOGRAM®" and insert -- RHOGAM® --.

Column 13, line 53, delete "to umors," and insert -- to tumors, --.

Column 14, line 38, delete "( 1994)" and insert -- (1994) --.

Column 14, lines 65-67, delete "Combining *Clostridium perfringens* and Clostridium histolyticumCollagenages to Treat Conditions with Excess Connective Tissue Formation" and insert as a new paragraph and section heading -- Combining *Clostridium perfringens* and *Clostridium histolyticum* Collagenases to Treat Conditions with Excess Connective Tissue Formation --.

Column 15, line 46, delete "Use of a chimeric" and insert -- Use of a Chimeric --.

Column 20, line 8, delete -- 1 x $10^6$" and insert -- 1 x $10^{-6}$ --.

Column 20, line 59, delete "attending physician., based" and insert -- attending physician, based --.

UNITED STATES PATENT AND TRADEMARK OFFICE
CERTIFICATE OF CORRECTION

PATENT NO. : 5,562,907

DATED : Oct. 8, 1996

INVENTOR(S) : Stephen S. Arnon

It is certified that error appears in the above-indentified patent and that said Letters Patent is hereby corrected as shown below:

In the Specification:

Column 21, line 53, delete "the life of" and insert -- the lifetime of --.

Column 21, line 62 delete "joint capsule-" and insert -- joint capsule --.

Column 22, line 20, delete "("leakage" )" and insert -- ("leakage") --.

Column 22, line 21, delete "site other" and insert -- site into other --.

Column 22, line 27, delete "New Checks Use of Color Meurotoxin and" and insert -- Use of Cobra Neurotoxin and --.

Column 22, line 37, delete "patients a additional means" and insert -- patients an additional means --.

In the Claims

Column 23, line 23, delete "is a natural toxin, a" and insert -- is a natural toxin or a fragment thereof, a --.

Signed and Sealed this

Thirteenth Day of May, 1997

Attest:

BRUCE LEHMAN

*Attesting Officer* *Commissioner of Patents and Trademarks*